United States Patent [19]

Pfeiffer

[11] Patent Number: 5,677,537
[45] Date of Patent: Oct. 14, 1997

[54] DEVICE FOR RECORDING IMAGES IN THE ORAL CAVITY ESPECIALLY FOR DENTAL DIAGNOSIS

[76] Inventor: Manfred Pfeiffer, 18, Warrington Crescent, GB-London W9 1EL, England

[21] Appl. No.: 630,933

[22] Filed: Apr. 5, 1996

[30] Foreign Application Priority Data

Apr. 5, 1995 [DE] Germany ................ 29505854 U

[51] Int. Cl.⁶ .................................................. A61B 6/14
[52] U.S. Cl. ................. 250/370.09; 378/170; 378/191
[58] Field of Search ..................... 250/370.09; 378/98.8, 378/168, 169, 170, 189, 191

[56] References Cited

U.S. PATENT DOCUMENTS

| 4,707,847 | 11/1987 | Van Aken | 378/170 |
| 5,434,418 | 7/1995 | Schick | 250/370.09 X |

FOREIGN PATENT DOCUMENTS

| 0279955 | 8/1988 | European Pat. Off. . |
| 0397599 | 11/1990 | European Pat. Off. . |
| 0544974 | 6/1993 | European Pat. Off. . |
| 8029528 | 11/1980 | Germany . |
| 9419116 | 3/1995 | Germany . |

*Primary Examiner*—Edward J. Glick
*Attorney, Agent, or Firm*—Robert W. Becker & Associates

[57] ABSTRACT

A device for recording an image in the oral cavity has a sensor with a housing having two main surfaces. The sensor includes an image recording layer positioned in the housing parallel and adjacent to one of the two main surfaces. A signal line is connected to the housing at one of the two main surfaces remote from the image recording layer. The signal line transmits signals of the image recording layer to a separate image processing and memory unit. A holder with a bite section and a receiving channel in which the sensor is received is provided. The holder has an abutment surface extending parallel to the two main surfaces. The abutment surface has guide means for aligning the holder and the sensor relative to one another. A hose is slipped over abutment surface and sensor for fastening the sensor at the holder.

6 Claims, 1 Drawing Sheet

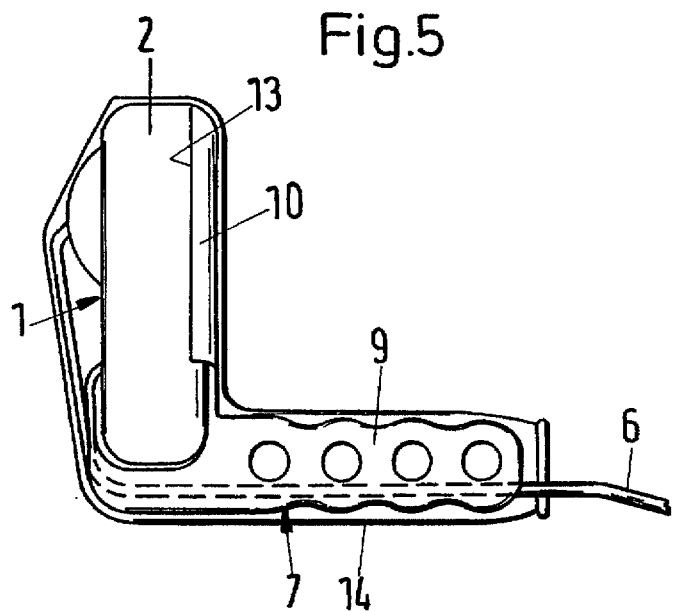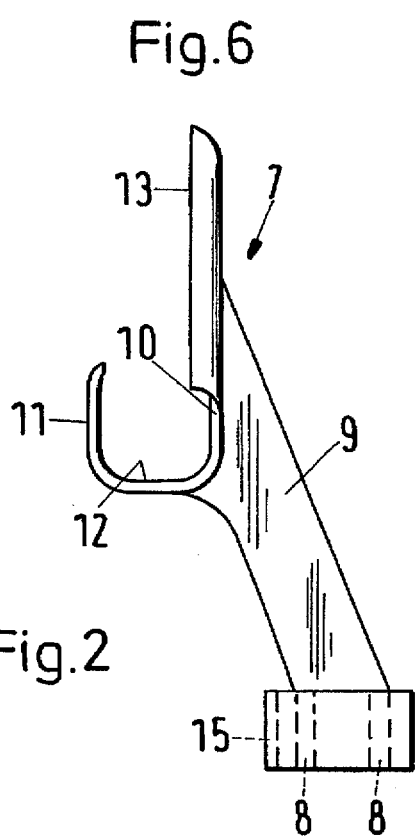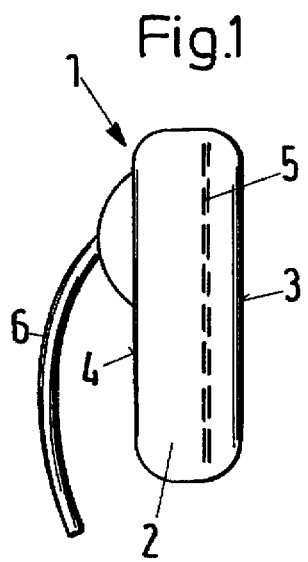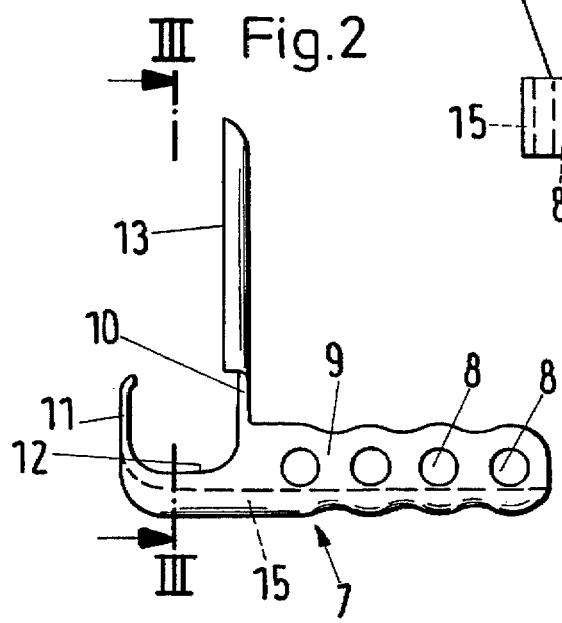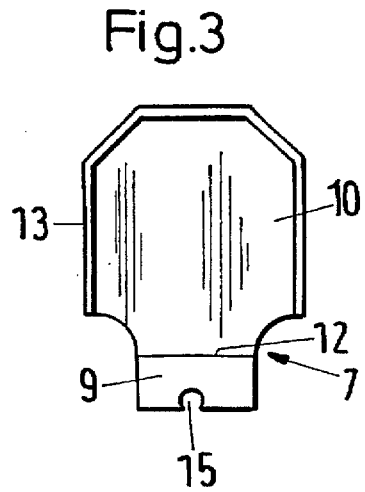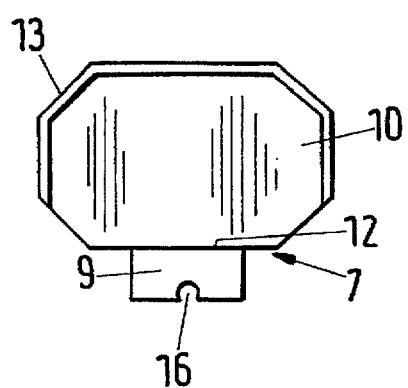

DEVICE FOR RECORDING IMAGES IN THE ORAL CAVITY ESPECIALLY FOR DENTAL DIAGNOSIS

BACKGROUND OF THE INVENTION

The present invention relates to a device for recording images in the oral cavity, especially for dental diagnosis, comprising a holder with a bite section into which a sensor is inserted which comprises a substantially rectangular sensor housing and an image recording layer which extend substantially parallel to one of the main surfaces of the housing. At the other main surface of the housing a signal line is guided out of the housing for transmitting the signals of the image recording layer to a separately arranged image processing and memory unit.

Such devices are known under the technical "intra-oral sensor". They are used by dentists in order to produce X-ray images of individual teeth or groups of teeth. For this purpose, the housing of the sensor is inserted into the patient's mouth and positioned behind the tooth or tooth group to be X-rayed whereby the imaging sensor which is embodied planar within the housing faces with its x-ray sensitive layer the tooth or the tooth group. Subsequently, irradiation with x-rays in a minimal dosage is performed from the exterior. The optical impulses which are received by the imaging sensor are transmitted via a signal line extending from the housing to an external image processing and memory unit. This is, in general, a personal computer. In this manner x-ray images can be produced directly on location without any further delay and are immediately visible on the computer monitor. The dentist can then decide if any further images need to be recorded.

The various procedures in a dental practice are often very hectic and do not allow the user enough time to deal with technically complicated devices or solutions. In this context it is often more advantageous to provide a simple solution or design whose functioning is immediately obvious to the user.

It is therefore an object of the present invention to provide a device for image recording in the oral cavity which, with respect to the often hectic procedures in a dental practice or dental clinic, is especially user-friendly.

SUMMARY OF THE INVENTION

A device for recording an image in the oral cavity according to the present invention is primarily characterized by:
- a sensor comprising a housing with two main surfaces;
- the sensor including an image recording layer positioned in the housing parallel and adjacent to one of the two main surfaces.
- a signal line connected to the housing at one of the two main surfaces remote from the image recording layer, the signal line transmitting signals of the image recording layer to a separate image processing and memory unit;
- a holder comprising a bite section and a receiving channel in which the sensor is received;
- the holder having an abutment surface extending parallel to the two main surfaces, the abutment surface having guide means for aligning the holder and the sensor to one another;
- a hose slipped over the abutment surface and the sensor for fastening the sensor at the holder.

Advantageously, the guide means is an edge of the abutment surface projecting toward the sensor and matching the contour of the housing of the sensor.

Preferably, the edge has an outer surface are a facing away from the housing and the outer surface area is rounded.

Advantageously, the abutment surface is radiolucent for x-rays and the housing rests at the abutment surface with the main surface adjacent to which the image recording layer is positioned.

Preferably, the bite section of the holder has a passage for the signal line. The passage is preferably a channel extending along one longitudinal side of the bite section. The signal line is secured by the channel walls of the channel.

According to the present invention, the holder is provided with an abutment surface which extends parallel to the main surfaces of the sensor housing and is provided with guide means for at least initially aligning the holder and the sensor relative to one another and by providing a hose which, for a final fastening of the sensor at the holder, is slipped over both the abutment surface and the sensor.

Such a device includes only a small number of parts and is comprised only of a holder with bite section, a sensor, and a hose to be slipped over sensor and holder. The hose, for hygienic reasons, is already present in a dental practice or dental clinic. In the present invention it takes over the additional task of a final fastening means of the sensor at the holder after a prelimanary alignment of these parts relative to one another has been achieved with guide means positioned at the abutment surface of the holder. These guide means allow the user to immediately recognize how the sensor is to be positioned at the holder. The thus achieved prelimanary alignment of the parts relative to one another is subsequently fixed by slipping the hose over sensor and holder so that the device is then ready for use. The aforementioned steps for assembling the device are obvious from the structure of the individual parts so that the assembly, in the generally hectical work environment, can be performed without difficulties.

According to a further embodiment of the invention, the guide means is in the form of the edge of the abutment surface which projects in the direction of the sensor housing and which matches the contour of the sensor housing. For increasing the comfort of the device, the edge is softly rounded at its outer surface area.

Preferably, the abutment surface is radiolucent for x-rays and the sensor housing is positioned such that the main surface at which the image recording layer is positioned rests at the abutment surface. The correct insertion of the sensor into the oral cavity is thus additionally simplified.

In order to simplify the fastening of the signal line during insertion of the device into the oral cavity of the patient, the bite section of the holder can be provided with a passage for the signal line. Especially suitable is a passage in the form of a channel extending along the longitudinal side of the bite section whereby the signal line is clamped between the channel walls.

BRIEF DESCRIPTION OF THE DRAWINGS

The object and advantage of the present invention will appear more clearly from the following specification in conjunction with the accompanying drawings, in which:

FIG. 1 shows a side view of a sensor for image recording in the oral cavity having a signal line extending from the back side;

FIG. 2 shows a side view of a holder with bite section for receiving the sensor of FIG. 1:

FIG. 3 shows a part-sectional view of the holder of FIG. 2 along the line III—III of FIG. 2;

FIG. 4 shows in a view similar to FIG. 3 a further embodiment of a holder for a landscape imaging format;

FIG. 5 shows in a side view the device comprised of the sensor of FIG. 1 and the holder of FIG. 2 including the hose slipped over the tube parts for fixing the parts relative to one another; and FIG. 6 shows another embodiment of a holder with bite section for receiving the sensor of FIG. 1 in a representation corresponding to the view of FIG. 2.

DESCRIPTION OF PREFERRED EMBODIMENTS

The present invention will now be described in detail with the aid of several specific embodiments utilizing FIGS. 1 through 6.

The sensor 1 represented in FIGS. 1 and 5 is comprised of a sensor housing 2 with basic dimensions of approximately 28 mm×39 mm×7.5 mm. The sensor housing comprises two main surfaces 3, 4, two long narrow sides and two short narrow sides. In the vicinity of one of the main surfaces 3 an image recording layer that is sensitive to x-rays is arranged within the sensor housing 2. Via a signal line 6 in the form of a flexible cable the signals of the image recording layer 5 can be guided into a non-represented image processing and memory unit. Also not represented in the drawing is the x-ray source which acts in the direction toward the image recording layer 5. The sensor is used such that it is inserted into the oral cavity of a patient with the image recording layer 5 facing the teeth to be x-rayed so that the portion of the jaw to be x-rayed is positioned between the x-ray source and the image recording layer 5. The exact positioning of the axis of the x-ray source on the one hand and of the image recording layer 5 on the other hand can be performed with suitable centering devices.

These centering devices are connected to the sensor holder 7. The holder 7 for this purpose is provided with a plurality of transverse bores 8 into which the centering devices can be laterally inserted.

The holder 7 represented in FIG. 2 is of a one-part construction and comprises a bite section 9, an abutment member with abutment surface 10 extending at a right angle to the bite section 9, and a clamping section 11. The clamping section 11 together with the oppositely arranged abutment surface 10 provides a receiving channel 12 into which the sensor 1 can be inserted. Upon insertion of the sensor 1 a preliminary alignment of the sensor 1 and the holder 7 occurs. This is achieved, on the one hand, due to the elasticity of the elastic clamping section 11 and, on the other hand, especially due to the design of the abutment surface 10. The abutment surface 10 is substantially flat and planar and has a size such that the inserted sensor 1 with its main surface 3 rests areally at the abutment surface 10 which is radiolucent for x-rays. For a lateral alignment of the sensor housing 2 relative to the holder 7 the abutment surface 10 is provided with an edge 13 projecting in the direction toward the sensor 1. The shape of the edge 13 matches the contour of the sensor housing 2 so that when the sensor 1 is inserted the abutment surface 10 with the edge 13 partly encloses the sensor housing 2 in order to center it.

FIG. 3 shows that the edge 13 does not extend about the entire periphery of the abutment surface 10, i.e., the lower end does not have an edge portion. Centering of the sensor in the downward direction is achieved by abutment of the corresponding narrow side of the sensor housing 2 at the receiving channel 12.

FIGS. 3 and 4 show two different holders 7. The holder of FIG. 3 serves for receiving a sensor 1 of an upright design, while the holder of FIG. 4 serves for receiving a sensor 1 for producing images in a landscape format.

The edge 13 of the abutment surface 10 serves as a preliminary fixation means of sensor 1 and holder 7 relative to one another. The final fastening is achieved with a hose 14 made of natural rubber which is slipped first over the abutment surface 10 and the sensor housing 2 and which is pulled preferably over the bite section 9. The own elasticity of the hose 14 is sufficient for pulling the sensor 1 securely against the abutment surface 10 so that the holder 7 and sensor 1 are secured in a defined alignment relative to one another.

The signal line 6 which is guided away from the sensor housing 2 from the second main surface 4 is guided through a channel 15 which is provided at the underside of the bite section 9. The signal line 6 is clamped between the channel walls 16.

In the holder 7 represented in FIG. 6 the abutment surface 10 and the bite section 9 are not positioned at a right angle to one another, but the bite section 9 is positioned at a slant to the abutment surface 10 for the sensor 1. This holder 7 is designed for use in the molar area and especially suitable for image recording of molars.

The present invention is, of course, in no way restricted to the specific disclosure of the specification and drawings, but also encompasses any modifications within the scope of the appended claims.

What I claim is:

1. A device for recording an image in the oral cavity, said device comprising:

a sensor comprising a housing with a first main surface and a second main surface;

said sensor including an image recording layer positioned in said housing parallel and adjacent to said first main surface;

a signal line connected to said housing at said second main surface, said signal line transmitting signals of said image recording layer to a separate image processing and memory unit;

a one-part holder comprising a bite section and a receiving channel in which said sensor is received;

said holder having an abutment member, wherein said bite section and said receiving channel are located on opposing sides of said abutment member and wherein one of said opposing sides neighboring said receiving channel is an abutment surface for said sensor;

said abutment surface extending parallel to said first and second main surfaces and having guide means for aligning said holder and said sensor to one another;

a hose slipped over said abutment member and said sensor for fastening said sensor at said holder.

2. A device according to claim 1, wherein said guide means is an edge of said abutment surface positioned at least at a side of said abutment surface remote from said receiving channel and projecting toward said sensor and matching the contour of said housing of said sensor.

3. A device according to claim 2, wherein said edge has an outer surface area facing away from said housing and wherein said outer surface area is rounded.

4. A device according to claim 1, wherein said abutment member is radiolucent for X-rays and wherein said first main surface rests at said abutment surface.

5. A device according to claim 1, wherein said bite section of said holder has a passage for said signal line.

6. A device according to claim 5, wherein said passage is a channel extending along one longitudinal side of said bite section, wherein said signal line is secured by channel walls of said channel.

* * * * *